United States Patent [19]

Müller

[11] Patent Number: 5,176,917
[45] Date of Patent: Jan. 5, 1993

[54] TRANSDERMAL SYSTEM EXHIBITING GRADUATED DRUG RELEASE AND ITS USE FOR THE LOCAL OR SYSTEMIC ADMINISTRATION OF ACTIVE SUBSTANCES

[75] Inventor: Walter Müller, Neuwied, Fed. Rep. of Germany

[73] Assignee: LTS Lohmann, Neuwied, Fed. Rep. of Germany

[21] Appl. No.: 730,023

[22] Filed: Jul. 12, 1991

Related U.S. Application Data

[63] Continuation of Ser. No. 492,530, Mar. 12, 1990, abandoned.

[30] Foreign Application Priority Data

Mar. 15, 1989 [DE]  Fed. Rep. of Germany ....... 3908431

[51] Int. Cl.⁵ ............................................. A61F 13/02
[52] U.S. Cl. .................................. 424/448; 414/447; 414/449
[58] Field of Search ...................... 424/448, 449, 447

[56]  References Cited

U.S. PATENT DOCUMENTS 4,834,979  5/1989  Gale .................................... 424/448
4,917,895  4/1990  Lee et al. ............................ 424/448

Primary Examiner—Thurman K. Page
Assistant Examiner—Leon R. Horne
Attorney, Agent, or Firm—Sprung, Horn Kramer & Woods

[57]  ABSTRACT

The present invention relates to a transdermal system with graduated drug release and to its use for the local or systemic dermal drug administration in human and veterinary medicine, or in cosmetics.

4 Claims, 5 Drawing Sheets

FIG.1
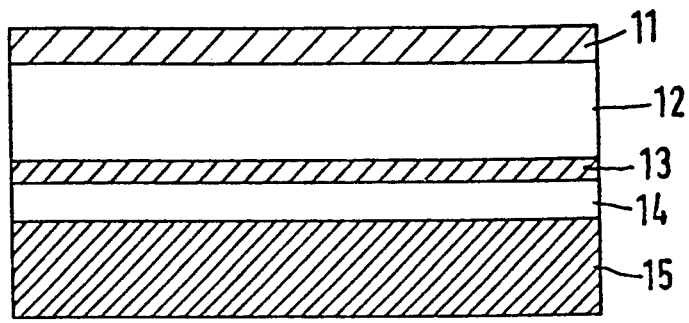
FIG.2
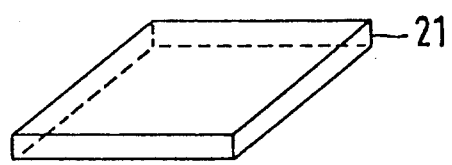
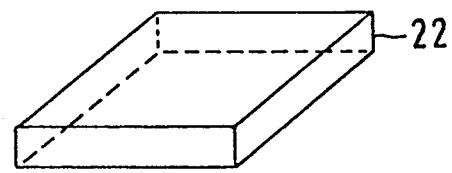
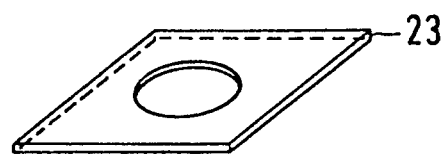
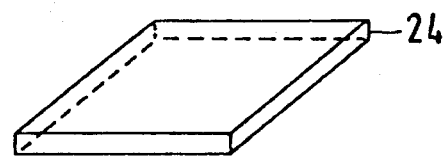
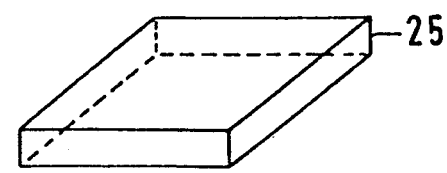

FIG.3
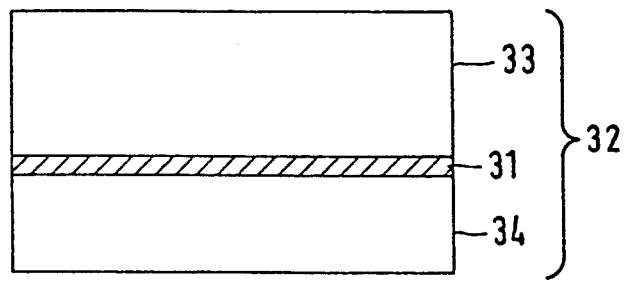
FIG.4
4.1
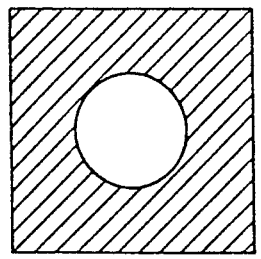
4.2
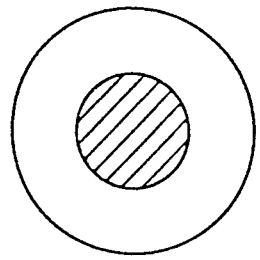
4.3
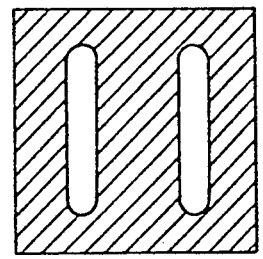
4.4
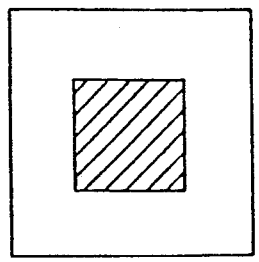
4.5
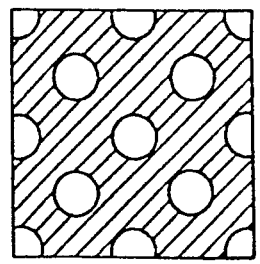
4.6
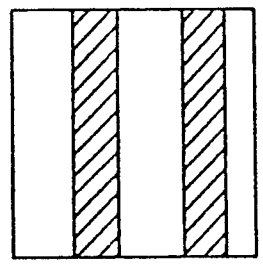

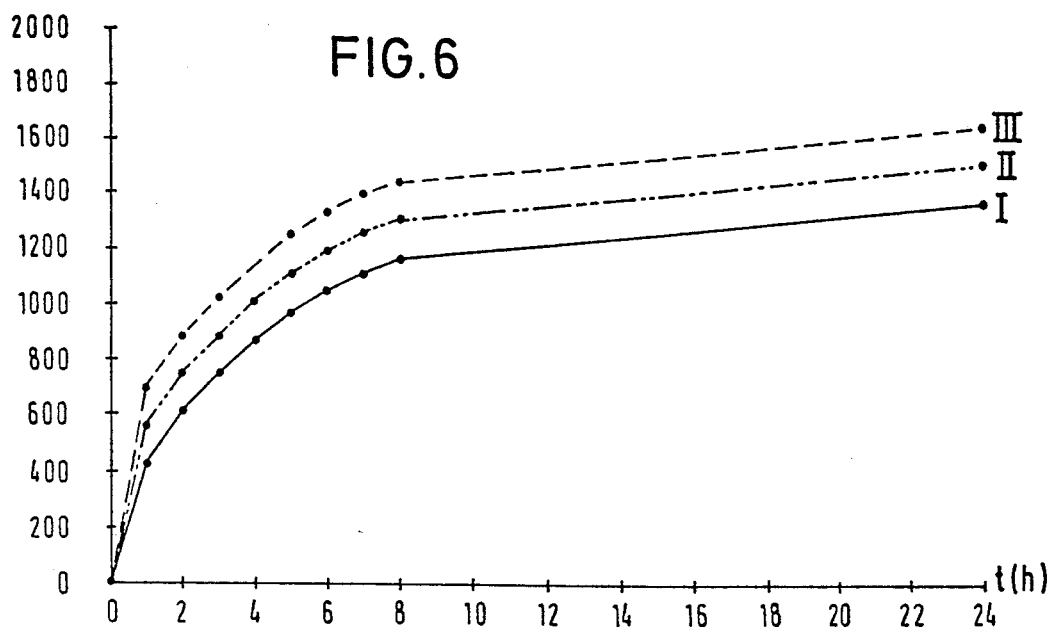
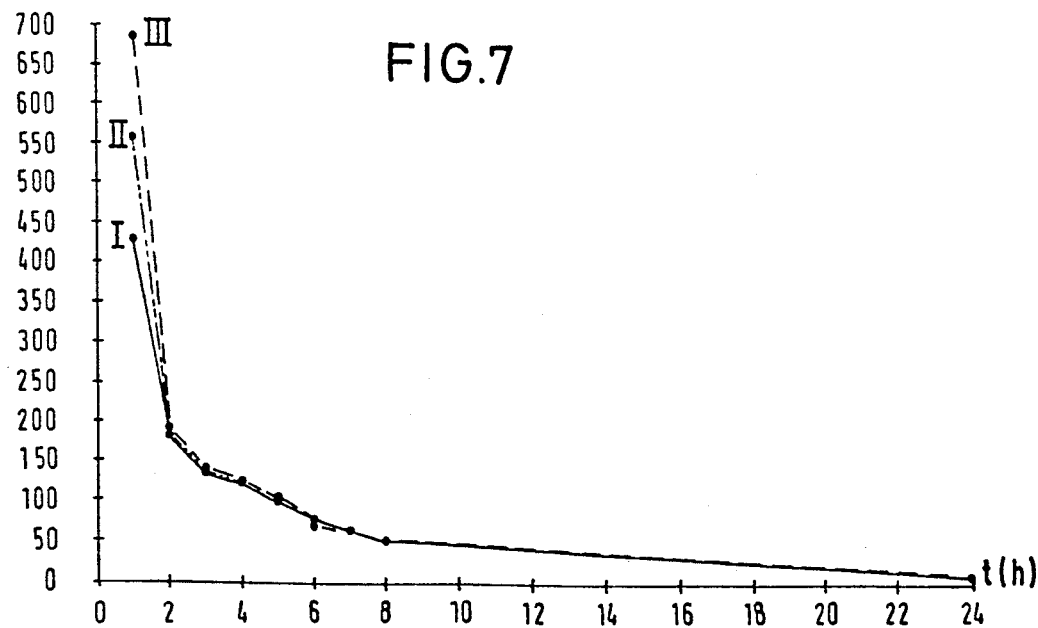

TRANSDERMAL SYSTEM EXHIBITING GRADUATED DRUG RELEASE AND ITS USE FOR THE LOCAL OR SYSTEMIC ADMINISTRATION OF ACTIVE SUBSTANCES

This application is a continuation of application Ser. No. 492,530, filed Mar. 12, 1990, now abandoned.

The present invention relates to a transdermal system with graduated drug release and to its use for the local or systemic dermal drug administration in human and veterinary medicine, or in cosmetics.

Transdermal therapeutic systems have become well-established in the treatment of various diseases. Their major advantage is the fact that the active substance after permeation through the skin is immediately systemically effective, thereby avoiding the primary liver passage which always occurs in the case of orally administered active substances, and that very constant plasma levels can be achieved, if the system is adequately prepared. This is of special importance for active substances which exhibit short half-lives and therefore make necessary a constant fresh delivery of the drug.

Since the system is applied externally, the intended function can thus be performed for a very long period of time—some of the commercially available systems may remain on the site of application for up to one week. This effect can virtually not be achieved with oral systems, since they leave the organism after one day at the latest due to digestion.

Such transdermal systems usually consist of a backing layer which is impermeable to the active substance, an active substance reservoir, a fixing device for anchoring the system to the skin, and a removable protective foil for the skin side of the system. In a preferred embodiment of the fixing device the skin side is rendered at least partially self-adhesive.

In those systems the reservoir may have the form of a bag containing the liquid or dissolved active substance, or it may be a foil-like article comprising the active substance as a polymer containing preparation.

The latter systems are also called matrix systems, and the following statements relate to those kinds of systems.

If the reservoir of such a matrix system consists of only one homogeneous layer and no further layers controlling the active substance release are present between the side facing the skin after application and the skin itself, the system controls the active substance release; if the matrix is supersaturated this is performed according to equation 1, if this is not the case according to equation 2.

$$Q = (D_{DR} \cdot [C_{DR} - C_{SDR}] \cdot C_{SDR} \cdot t)^{\frac{1}{2}} \quad \text{equation 1}$$

$$Q = 2 \cdot C_{DR} \cdot (D_{DR} \cdot t / 3.14)^{\frac{1}{2}} \quad \text{equation 2}$$

Q: amount of active substance released at time t
t: time
$D_{DR}$: diffusion coefficient of active substance in the matrix
$C_{DR}$: active substance concentration in the reservoir
$C_{SDR}$: saturation solubility of the active substance in the reservoir Since Q is directly proportional the square root of time, these equations are also called the root-t-law.

The active substance release is not constant in these systems and rapidly decreases in the course of time.

If a more constant active substance release is desired, this can be achieved by the use of so-called controlling membranes.

Such a system consists of a backing layer, an active substance reservoir, a controlling membrane, a pressure-sensitive adhesive layer for securing the system to the skin and a removable protective foil.

$$Q = C_0 \cdot e^{-D/l \cdot t} \quad \text{equation 3}$$

$C_0$ = initial concentration of active substance
D = diffusion coefficient of active substance in the membrane
l = thickness of membrane For some groups of active substances constant release rates and constant plasma levels may be undesired. For example, in the case of blood pressure and circulation influencing agents, calmatives and soporifics, psychopharmacological agents, anodynes, angina pectoris agents, antiasthmatics, and agents facilitating the curing of drug addiction, e.g., nicotine. In case of these substances it is advantageous to achieve plasma levels adapted to the indiviual need.

In addition, some drugs are not administered constantly, but only when need arises at probably very large intervals. Such a substance which is already on the market as transdermal system, e.g., is scopolamine against motion sickness.

Other active substances suitable for such a temporary administration, e.g., are anodynes, psychopharmacological agents, calmatives, soporifics, or appetite-suppressing agents.

In the case of a transdermal application of such substances, the transdermal system has to effect a variable active substance flux through the skin during the period of application, whereby an initial dosage provides for a rapid commencement of effect, and a maintenance dosage provides for a sufficiently long constancy or a preprogrammed decrease of plasma levels.

A transdermal therapeutic system to solve this problem has been described in EP-A 0 227 252. In this case, the active substance in a reservoir is brought into contact with an amount of penetration accelerator merely sufficient to maintain the accelerated penetration only during a defined initial phase of application. It is of disadvantage in this case that each active substance has to assigned a suitable penetration accelerator.

Another solution to this problem has been proposed in DE-OS 36 42 931. In this case, at least two plaster chambers lying side by side and being separate from each other are provided with different active substance concentrations so that in the first application phase the release of active substance from all chambers effects a high initial dosage, while after evacuation of the chambers with low active substance concentration only those chambers with higher active substance concentration contribute to the release and thus effect a lower maintenance dosage. This system is expensive merely because of this chamber construction, and requires special measures with respect to the different adjustments of concentration in the chambers.

It is accordingly the object of the present invention to provide a plaster used as therapeutic system with graduated drug release for the administration of active substances to the skin, which avoids the compelling presence of a penetration accelerator and—in excess of the prior art—offers additional possiblities to control the active substance release, and which furthermore can be manufactured in a simple manner.

According to the present invention, this object is surprisingly achieved in that the active substance containing reservoir comprises at least one membrane located parallel to the releasing surface, the surface of said membrane being smaller in its dimension than the releasing area.

Thus the subject matter of the present invention is a transdermal system for the controlled, gradational administration of active substances to the skin, which exhibits a high initial dosage and a lower maintenance dosage and consists of a backing layer averted from the skin and impermeable to active substances, an active substance reservoir which comprises at least one membrane located parallel to the releasing surface, a pressure-sensitive adhesive fixing device for securing the system to the skin, and a removable protective layer optionally covering the surfaces of the system facing the skin, wherein the membrane surface is smaller than the releasing surface of the system.

In this connection, a membrane means an areal flexible article whose permeability to components of the active substance reservoir can also equal nil. Thus, for example, a thin metal foil is also comprised by the term membrane. Usually the thickness of such a membrane rarely ecxeeds 50μ, however, thicker membranes are not excluded for special cases.

Normal membrane thicknesses are from 20 to 100 μm.

The membrane may either be incorporated or embedded in the membrane, or adjoin the reservoir on the skin side.

According to an embodiment of the present invention, the membrane is impermeable to the active substance or substances to be released. According to a further embodiment, the membrane exhibits a limited permeability to the active substance or active substances. According to the present invention it is also possible to combine two membranes having different permeabilities to the substances to be released. In this connection, at least one of these membranes has a smaller surface than that of the releasing area of the system. In this case it is of advantage that said smaller membrane is impermeable to the substance or substances to be released, and incorporated in the reservoir.

The active substance or substances may be present in the reservoir at a concentration below the saturation concentration or at a concentration exceeding the saturation concentration.

The reservoir itself may consist of several layers of different composition.

In principle, the same materials as described for common systems can be used for all components of such a system. These materials are known to the man skilled in the art.

The backing layer may consist of flexible or inflexible material, and may be constructed single or multi-layered. Substances suitable for its production are polymeric substances, such as, e.g., polyethylene, polypropylene, polyethylene terephthalate, polyurethane, or polyamide. As further materials metal foils, e.g., an aluminum foil alone or coated with a polymeric substrate may be used. Textile fabrics may be used, too, if the components of the reservoir cannot leave the reservoir via the gas phase due to their physical properties.

In principle, the same materials may be used for the removable protective foil, however, they must additionally be rendered dehesive.

This dehesive preparation can be achieved by a special siliconization.

The reservoir or the layers of the reservoir, respectively, consist of a polymeric matrix and the active substance or substances, whereby the polymeric matrix exhibits such a self-adhesiveness that the coherence in case of a multi-layer construction is guaranteed. The polymeric material of the matrix may, e.g., be built up of polymers, such as rubber, rubber-like synthetic homo-, co-, or blockpolymers, polyacrylic acid esters and their copolymers, polyurethanes, copolymers of ethylene and polysiloxanes. In principle, all polymers are suitable which are used in the manufacture of pressure-sensitive adhesives and are physiologically acceptable. Additives may also be used, their nature depends on the polymer used and the active substance or substances. Depending on their function they can be divided into softeners, tackifiers, resorption agents, stabilizers, or fillers. Substances suitable for this purpose and physiologically acceptable are known to the man skilled in the art.

All physiologically acceptable foil-like materials having the adequate permeability to the active substance or substances or auxiliary agents, respectively, are suitable for the manufacture of the membranes. Membranes on the basis of polyethylene, polyamide, ethylene-vinyl acetate-copolymers, and polysiloxanes are particularly suitable.

BRIEF DESCRIPTION OF DRAWINGS

In the following, the invention is further illustrated but not limited by the drawings:

FIG. 1 shows a section through a system provided with a controlling membrane according to the prior art, FIG. 2 shows an embodiment of a system according to the present invention, FIG. 3 shows another view of the matrix of FIG. 2 with a membrane incorporated into the matrix, FIG. 4 in FIGS. 4.1 to 4.6 shows six different embodiments of the membrane, FIG. 7 shows the release behaviour of the same system as shown in FIG. 6, however, diagrammatically the active substance release rate per system and hour as function of time.

Figure 5A:
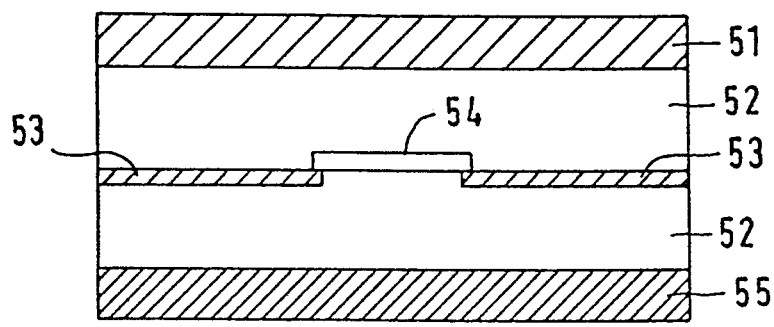
FIG. 5a shows a section through an embodiment of the present invention exhibiting a combination of an impermeable membrane with a membrane of higher permeability.

The system described in FIG. 1 consists of a backing layer (11), the active substance containing reservoir (12), the controlling membrane (13), a pressure-sensitive adhesive layer for securing the system to the skin (14), and a removable protective foil (15).

In some cases the pressure-sensitive adhesive layer (14) has the same formulation as the reservoir (12) so that the membrane is actually incorporated in the reservoir, and thus one can imagine the reservoir being built up of two parts.

If the active substance is present in the reservoir at an oversaturated concentration, a release according to a kinetic 0 is achieved by the membrane. Order, i.e., a constant release within the application period; and if the active substance is present below this concentration, a release according to a kinetic 1 is achieved. Order according to equation 3.

FIG. 2 shows the general construction of a system according to the present invention. It consists of a backing layer (21), a reservoir (22), a membrane (23), a self-adhesive skin coat (24), and a removable protective foil (25).

Membrane (23) is smaller than the reservoir surface, since the membrane has a central, circular recess.

In FIG. 3 a membrane (31) is incorporated in the reservoir (32) which for this reason is divided into two halves (33 and 34). If the reservoir formulation is self-adhesive, the self-adhesive skin coat (24) of FIG. 2 can naturally be omitted. Due to the fact that the surface of the membrane is always smaller than the total area of the reservoir, reservoir and skin, or reservoir and pressure-sensitive adhesive layer, or both parts of the reservoir, respectively, are in direct contact with each other on that surface which is not covered by the membrane.

FIG. 4 shows some examples of geometric forms of such membranes according to the present invention, in which either the hatched areas or the areas without hatches are membranes.

The embodiments according to the present invention as shown in FIGS. 3 and 4 are particularly suitable for systems with only one membrane being impermeable to the active substance, e.g., such as is shown in FIG. 4.1 and integrated into the reservoir according to FIG. 3.

At first, this system behaves like a common matrix system, i.e., the active substance is released over the whole releasing surface according to the so-called root-t-law. However, as soon as the reservoir member, which is positioned below the membrane area, is emptied so far that the depletion zone has reached the membrane, the behaviour of the reservoir compared to a common matrix system changes drastically. The active substance release decreases rapidly on the surface having the same dimension as the membrane, while on the partial surface which is not covered by the membrane the release continues undiminishedly according to the root-t-law until the depletion zone reaches the backing layer. Thus, the additional initial dosage originates from the area lying below the membrane. By way of changing the absolute area sizes and the relation between membrane surface and total surface of the reservoir, the amount of initial dosage and maintenance dosage can be influenced within wide ranges.

As a matter of fact, such a release behaviour can also be achieved in that the reservoir is given a steplike geometry. However, this bears the disadvantage that such a system is more difficult to produce, and that due to the plastic deformability of usual reservoir formulations such a system does not maintain its steplike shape.

Embodiment 4.5 is particularly advantageous, since there are no problems concerning positioning due to the variety of holes within the membrane.

By way of changing the ratio of membrane surface to the total surface, and the choice of membranes of different permeabilities to the active substance, the release behaviour of the system can be influenced in wide ranges, as is stated below. It is particularly possible administer very high initial dosages.

Figure 5B:
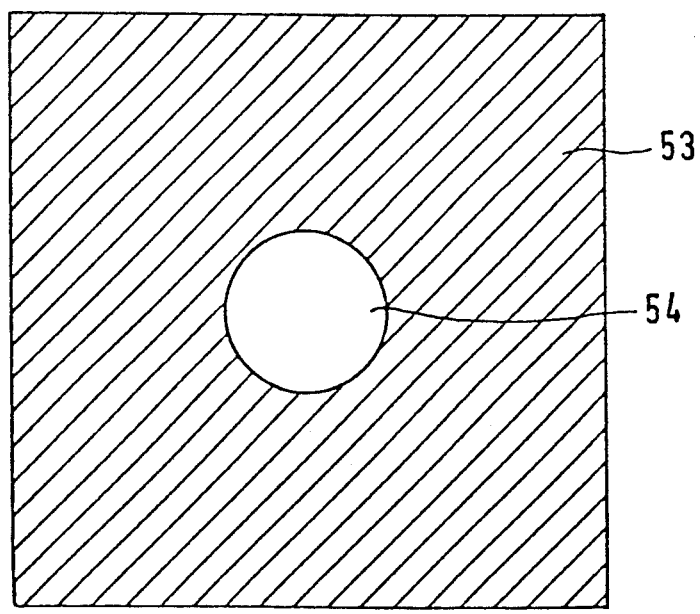
FIG. 5b shows a top view on the embodiment of FIG. 5a, FIG. 6 shows diagrammatically the release behaviour of an embodiment with a membrane incorporated in the reservoir and impermeable to the active substance in the form as shown in FIG. 4, whereby the cumulated released amount of active substance is shown as function of time.

FIGS. 5a and 5b show in sectional view and in top view an embodiment of the present invention which is provided with a combination of two different membranes. The combination of a membrane having permeability "0" with a membrane of higher permeability is particularly suitable. Such a system is shown in FIG. 5a. It consists of the impermeable backing layer (51), the reservoir (52), a membrane of permeability 0 to the active substance or substances (53), a membrane of a higher permeability than 0 to the active substance or substances (54), and a removable protective layer (55).

Both membranes are once more shown in FIG. 5b in top view. As a matter of fact, the membrane having permeability 0 must be smaller than the total releasing surface of the system, thus limiting the maximum active substance release on that partial area of the total releasing surface corresponding to the membrane size, since that portion of active substance lying above the membrane cannot pass it.

The membrane having the permeability higher than 0 effects an active substance release according to a kinetic of order 0 or 1 on that partial area of the total releasing surface corresponding to its size.

Both membranes need not necessarily lie in the same plane within the system. Their exact position depends on the individual requirements, and it is an additional means to achieve the desired release behaviour.

If the membrane having permeability 0 lies closer to the releasing surface, the other membrane may be as large as the total releasing surface without changing the release behaviour, since said membrane is of no effect, if it lies above the impermeable membrane.

FIGS. 6 and 7 show the release behaviour of those systems having a membrane which is impermeable to the active substance, as example a scopolamine plaster is chosen. The following indications apply to all samples described in the following: the active substance content amounts to 450 $\mu g/cm^2$ and the weight per unit area of the self-adhesive reservoir amounts to 12.5 $mg/cm^2$.

FIG. 6 shows the cumulated released amount of scopolamine as function of time.

Curve I corresponds to a normal system of 2 $cm^2$ size without membrane, and serves as comparison.

Curve II corresponds to a system of a total size of 3 $cm^2$; an impermeable membrane is incorporated into the reservoir. The membrane has an area of 1 $cm^2$ and divides the reservoir into one layer having an area weight of 10.4 $mg/cm^2$ and one having an area weight of 2.1 $mg/cm^2$.

Curve III corresponds to a system of a total area of 4 $cm^2$ and a membrane surface of 2 $cm^2$.

It can clearly be recognized that on the whole the active substance release of the systems provided with membrane is higher. However, in FIG. 7 it can be recognized more clearly that this increased active substance release only applies to the initial phase of release. FIG. 7 shows the release rate per system and hour as function of time, i.e., the flux is indicated.

Thus, this system is particularly useful, if relatively high initial dosages shall be combined with a maintenance dosage which is not necessarily constant.

Figure 8:
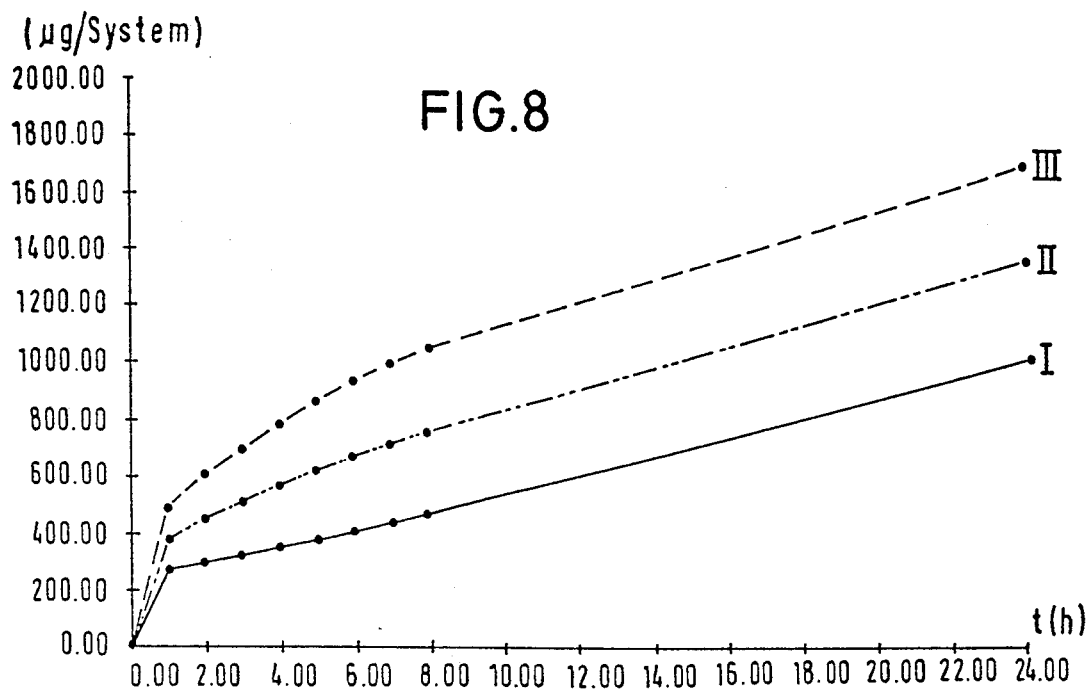
FIG. 8 shows in a diagram the release behaviour of a system according to the present invention with a membrane of limited permeability to the active substance, whereby the cumulative active substance release is plotted versus time.
Figure 9:
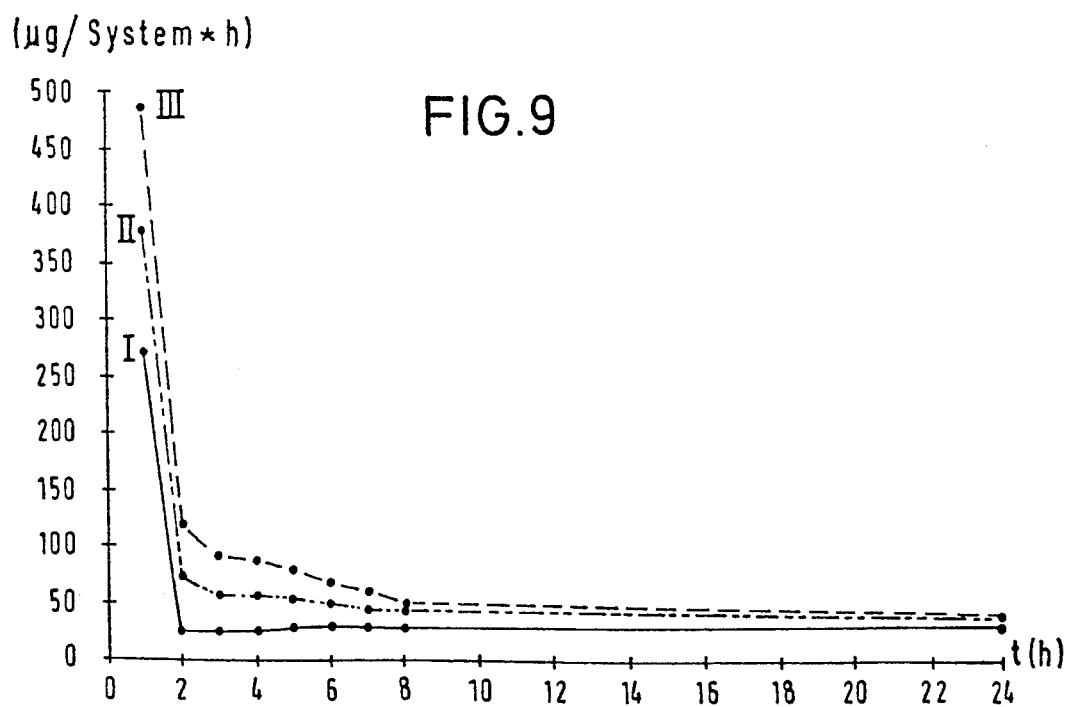
FIG. 9 shows diagrammatically the release rate of the same system as shown in FIG. 8 per system and hour as function of time.

FIGS. 8 and 9 show an embodiment according to the present invention having a membrane of limited permeability to the active substance; as example a scopolamine plaster was used under the same conditions as described for FIGS. 6 and 7.

The cumulative release is shown in FIG. 8, the flux is shown in FIG. 9. Curve I or flux I, respectively, corresponds to a system of 2 cm² having a membrane of the same size (comparison), curve II or flux II, respectively, correspond to a system of 2.5 cm² having a membrane of 2 cm², and curve III or flux III, respectively, correspond to a system of 3 cm² size having a membrane of 2 cm².

Even the system according to curve I and flux I is able to release a certain initial dosage. This initial dosage corresponds to a release according to the root-t-law according to equation 1 and 2, which takes place until the depletion zone of the active substance has reached the membrane.

The other two systems provided with membrane, which are of smaller dimension than the releasing surface of the system the initial dosage can be increased very easily. In this case, the intitial dosage is followed by a constant maintenance dosage the amount of which depends on the permeability and the surface of the membrane.

Production of the systems according to the present invention used in FIGS. 6 to 9 (samples)

230 g polyacrylate resin adhesive (50% in acetic ester)
  6 g scopolamine base
  10 g Cetiol S
  50 g methanol were mixed and the mixture homogenized.

A siliconized polyester foil of 100μ thickness was coated with this mixture as films of 400μ (film I) and 100μ (film II), the films were dried at 50° C. for 15 minutes. After drying, film I had a weight per unit area of 103 g/m² and film II one of 21 g/m².

The membrane having circular recesses of adequate size was laminated on film II, and film I in turn was laminated thereon. The siliconized polyester foil of film I was removed and substituted for an unsiliconized foil of 15μ thickness.

The individual samples were punched in such a way that the adequate total area resulted and the recess became positioned centrally.

Performance of the in vitro-release

The release was carried out at 32° C. according to the paddle-over-disk-method using 50 ml physiological saline. In order to determine the samples the total release medium was changed completely and the content determined according to a HPLC-method.

I claim:

1. A transdermal system for the controlled administration of an active substance to the skin, which exhibits a high initial dosage and a lower maintenance dosage and consists of:
   (A) a backing layer impermeable to the active substance and, in use, to be spaced from the skin,
   (B) a reservoir having two portions,
      (i) a first active substance portion adjacent the backing layer, and
      (ii) a second active substance portion having a predetermined releasing surface for the active material,
   (C) a pressure-sensitive adhesive for securing the second active substance reservoir portion to the skin, and
   (D) a membrane between the first and second active substance reservoir portions, the membrane being permeable to the active substance and including openings through which the active substance can pass, the surface area of said openings being smaller than the releasing surface area of the second reservoir portion, whereby the second reservoir portion initially releases its active material to the skin while the flow of active material from the first to the second reservoir portion is restricted by the membrane, so that there is an initial high rate of transfer of active material followed by a lower controlled rate of transfer.

2. A transdermal system according to claim 1, wherein the membrane is impermeable to the active substance and includes openings through which the active substance can pass.

3. A transdermal system according to claim 1, wherein the membrane is of limited permeability to the active substance.

4. A transdermal system according to claim 1, wherein the concentration of active substance in the first reservoir portion differs from that in the second reservoir portion.

* * * * *